US009784693B2

United States Patent
Karim et al.

(10) Patent No.: US 9,784,693 B2
(45) Date of Patent: Oct. 10, 2017

(54) APPARATUS FOR RADIATION DETECTION IN A DIGITAL IMAGING SYSTEM

(71) Applicants: Karim S. Karim, Waterloo (CA); Sina Ghanbarzadeh, Kitchener (CA)

(72) Inventors: Karim S. Karim, Waterloo (CA); Sina Ghanbarzadeh, Kitchener (CA)

(73) Assignee: DOSE SMART IMAGING, Waterloo, Ontario (CA)

( * ) Notice: Subject to any disclaimer, the term of this patent is extended or adjusted under 35 U.S.C. 154(b) by 0 days.

(21) Appl. No.: 15/209,864

(22) Filed: Jul. 14, 2016

(65) Prior Publication Data

US 2017/0018588 A1    Jan. 19, 2017

Related U.S. Application Data

(60) Provisional application No. 62/192,110, filed on Jul. 14, 2015.

(51) Int. Cl.
| | |
|---|---|
| *H01L 31/115* | (2006.01) |
| *G01N 23/04* | (2006.01) |
| *A61B 6/00* | (2006.01) |
| *H01L 51/00* | (2006.01) |
| *G01T 1/24* | (2006.01) |

(52) U.S. Cl.
CPC .......... *G01N 23/04* (2013.01); *A61B 6/4233* (2013.01); *G01T 1/24* (2013.01); *H01L 51/00* (2013.01)

(58) Field of Classification Search
CPC ......... H01L 27/14663; H01L 27/14609; H01L 27/1462; H01L 27/14623; H01L 27/14685; H01L 27/14689

USPC .......................................................... 257/429
See application file for complete search history.

(56) References Cited

U.S. PATENT DOCUMENTS

| | | | |
|---|---|---|---|
| 4,233,514 A | 11/1980 | Kingsley | |
| 5,880,472 A | 3/1999 | Polischuk et al. | |
| 6,097,748 A * | 8/2000 | Huang | H01S 5/0262 372/50.124 |
| 6,373,062 B1 | 4/2002 | Ghelmansarai | |
| 6,806,473 B2 | 10/2004 | Honda et al. | |
| 7,256,402 B1 | 8/2007 | Lee | |
| 7,615,731 B2 | 11/2009 | Heiler et al. | |
| 9,269,838 B2 | 2/2016 | Karim et al. | |
| 2004/0178426 A1 | 9/2004 | Melekhov et al. | |

(Continued)

FOREIGN PATENT DOCUMENTS

| | | |
|---|---|---|
| JP | 2006156555 | 6/2006 |
| WO | 02067337 | 8/2002 |
| WO | 2010121386 | 10/2010 |

OTHER PUBLICATIONS

Canadian Intellectual Property Office as International Searching Authority, International Search Report and Written Opinion for PCT/CA2012/050881, Feb. 26, 2013.

(Continued)

*Primary Examiner* — Theresa T Doan
(74) *Attorney, Agent, or Firm* — Gowling WLG (Canada) LLP; Jeffrey W. Wong

(57) ABSTRACT

The disclosure is directed at a method and apparatus for producing a detector element. The detector element includes first and second electrodes located on opposites sides of a semiconductor layer. The first and second electrodes are staggered with respect to each other in a plane perpendicular to the semiconductor layer.

12 Claims, 14 Drawing Sheets

(56) References Cited

U.S. PATENT DOCUMENTS

| | | |
|---|---|---|
| 2007/0108398 A1 | 5/2007 | Imai |
| 2009/0026381 A1 | 1/2009 | Iwazaki |
| 2009/0026382 A1 | 1/2009 | Sakamoto et al. |
| 2009/0246402 A1 | 10/2009 | Mataki et al. |
| 2014/0346631 A1* | 11/2014 | Karim .................. H01L 31/085 257/435 |
| 2015/0001539 A1 | 1/2015 | Smith et al. |

OTHER PUBLICATIONS

United States Patent and Trademark Office, Office Action for U.S. Appl. No. 14/363,859, Aug. 19, 2015.

Ghanbarzadeh, et al., "Low dark current amorphous silicon Metal-Semiconductor-Metal photodetector for digital imaging applications", IEEE Electron Device Letters, Feb. 2014, vol. 35, No. 2.

Canadian Intellectual Property Office as International Searching Authority, International Search Report and Written Opinion for PCT Patent Application No. CA2016/050830, Oct. 6, 2016.

\* cited by examiner

US 9,784,693 B2

APPARATUS FOR RADIATION DETECTION IN A DIGITAL IMAGING SYSTEM

CROSS-REFERENCE TO RELATED APPLICATIONS

This application claims the benefit of U.S. patent application Ser. No. 62/192,110, filed Jul. 14, 2015, the contents of which are incorporated by reference.

FIELD OF THE DISCLOSURE

This disclosure relates generally to digital imaging systems, and more particularly to an apparatus for radiation detection in a digital imaging system.

BACKGROUND OF THE DISCLOSURE

Traditionally, X-ray diagnostic processes record x-ray image patterns on silver halide films. These systems direct an initially uniform pattern of impinging X-ray radiation through the object to be studied, intercept the modulated pattern of X-ray radiation with an X-ray radiation intensifying screen, record the intensified pattern on a silver halide film, and chemically transform the latent pattern into a permanent and visible image called a radiograph.

Radiographs are produced by using layers of radiation sensitive materials to directly capture radiographic images as modulated patterns of electrical charges. Depending on the intensity of the incident X-ray radiation, electrical charges generated either electrically or optically by the X-ray radiation within a pixel area are quantized using a regularly arranged array of discrete solid-state radiation sensors.

Recently, there has been rapid development of large area, flat panel, digital X-ray imagers for digital radiology using active matrix technologies used in large area displays. An active matrix includes a two-dimensional array (of which, each element is called a pixel) of thin film transistors (TFTs) made with a large area compatible semiconductor material. There are two general approaches to making flat-panel x-ray detectors, direct or indirect. The direct method primarily uses a thick photoconductor film (e.g. amorphous selenium) as the X-ray to electric charge converting layer coupled directly to the active matrix. In the indirect method, a phosphor screen or scintillator (e.g. CsI, GdOS etc.) is used to convert X-rays to light photons which are then converted to electric charge using an additional pixel level light sensor fabricated with the TFT on the active matrix array.

The key challenges with fabricating a vertical photodiode are the modifications required to the TFT fabrication process specifically, thick amorphous silicon layers, specialized p-doped contact layer and a complex reactive-ion etching (RIE) sidewall etching process to prevent optical crosstalk. These challenges reduce the fabrication yield and drive up the cost of manufacture. The key challenges with fabricating a lateral MSM photoconductor include the high dark currents at higher electric fields and photoresponse non-uniformity due to a non-uniform electric field. In addition, the lateral MSM photoconductor is not space efficient leading to low effective quantum efficiency (EQE). Each of these issues degrades imager performance, which is the key reason why MSM devices are not used in industry today for large area digital X-ray imaging.

SUMMARY OF THE DISCLOSURE

The present disclosure provides a system and method for an apparatus for radiation detection in a digital imaging system. The apparatus may be seen as a photoconductive element.

In one embodiment, the photoconductive element includes a lateral Metal-Insulator-Semiconductor-Insulator-Metal (MISIM) detector element. The insulator may also be seen as a blocking layer. The MISIM detector element can be coupled to a readout circuit element e.g. through a via in a dielectric layer that sits between the detector element and the readout circuit element.

In one embodiment, the apparatus includes a semiconducting layer to absorb incident photons and two electrodes coupled to the semiconducting layer located on opposite sides of the semiconducting layer. The two electrodes are preferably staggered with respect to each other. In a practical implementation, at least one of the electrodes is electrically isolated from the semiconducting layer using an insulator, or blocking layer. The insulated contact, or electrode, which is typically under high voltage bias, maintains a low dark current even under high electric field conditions. Applying the high electric field enables the apparatus, such as the MISIM detector, element to operate at a faster speed than conventional metal-semiconductor-metal (MSM) photoconductor designs and also to increase the collection efficiency (and hence EQE) of the electron hole pairs created by the photons impinging on the semiconducting layer. The structure of the present disclosure is simpler and correspondingly less expensive to manufacture in comparison to a traditional photodiode structure. Moreover, unlike traditional MSM photoconductors, the structure of the present disclosure yields higher performance because the readout circuit element can be embedded under the MISIM detector element yielding a larger area for light absorption. Also, putting the high voltage electrode away from the TFT electronics improves reliability. Moreover, the entire photoconductive element can be realized in a large area TFT display manufacturing process, which is more reliable and easier to access than the specialized process for a PIN photodiode. These and other advantages of the aspects of the present disclosure will be understood in conjunction with the following detailed description and accompanying drawings.

Therefore, there is provided a novel apparatus for radiation detection in a digital imaging system.

BRIEF DESCRIPTION OF THE DRAWINGS

Embodiments of the present disclosure will now be described, by way of example only, with reference to the attached Figures.

DETAILED DESCRIPTION

The present disclosure relates to an apparatus for radiation detection in a digital imaging system. The apparatus may include a photoconductive element that includes a detector element, such as a metal-insulator-semiconductor-insulator-metal (MISIM) detector element. In one embodiment, the detector element is integrated with a readout circuit element for a radiography imaging system.

In a preferred embodiment, the apparatus includes a pair of electrodes located on opposite sides of a semiconductor layer, the pair of electrodes staggered with respect to each other. In one embodiment, the pair of electrodes are spaced horizontally with respect to each other and do not overlap each other in a vertical plane. In another embodiment, the pair of electrodes are staggered with respect to each other in a plane perpendicular to the semiconductor layer.

Figure 1:
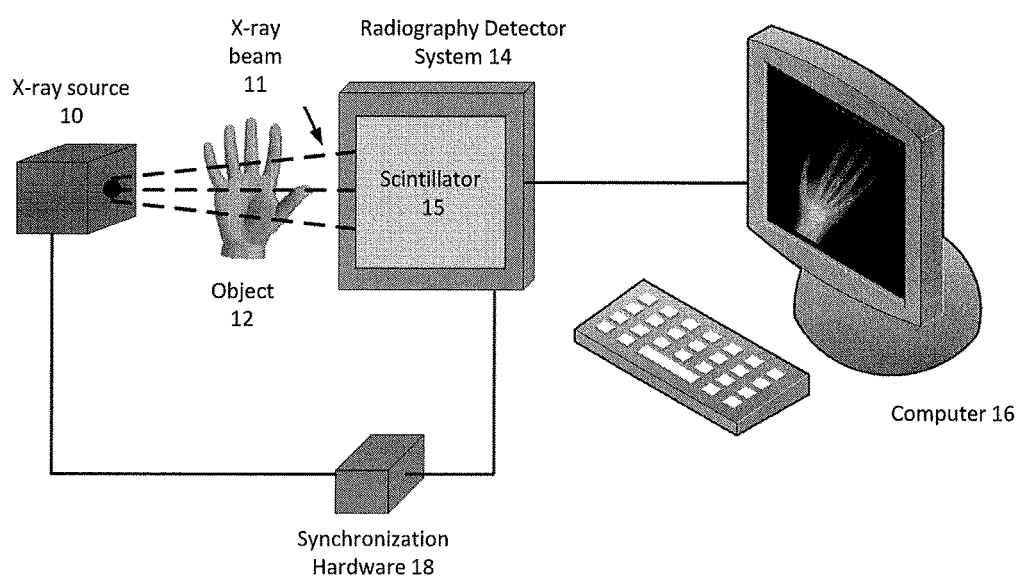
FIG. 1 illustrates a general diagram of a radiographic imaging environment in accordance with the present disclosure.

FIG. 1 illustrates a general diagram of a radiographic imaging environment. As shown, an X-ray source 10 generates an X-ray beam, or x-rays, 11 that is transmitted towards an object 12, e.g. a patient's hand, for imaging by a radiography detector system (RDS) 14. The results of the X-ray may be viewed on a computer 16. In the current embodiment, which may be seen as an indirect imaging system, the radiography detector system 14 includes a scintillator 15. In a direct imaging system, the x-rays 11 generate electronic charge within the radiography detector system 14 and there is no need for the scintillator 15.

For some radiography detector systems 14, synchronization hardware 18 is necessary to obtain the correct timing between the X-ray source 10 and the radiography detector system 14 that is sampling the impinging X-ray beam 11. In the present disclosure, the radiography detector system 14 includes a large area, flat panel detector based on active matrix technologies to achieve the imaging of object 12.

In general, the object 12 to be imaged is positioned between the radiation source 10 and the radiography detector system 14. X-rays 11, which pass through the object 12 interact with the radiography detector system 14. In indirect imaging, the x-rays 11 generate light photons as they pass through a phosphor screen or scintillator 15, such as structured Cesium Iodide (CO, Gadolinium oxysulfide (GOS) or Calcium Tungsten Oxide (CaWO4). These indirectly generated light photons then further generate electronic charge within the radiography detector system 14.

Figure 2:
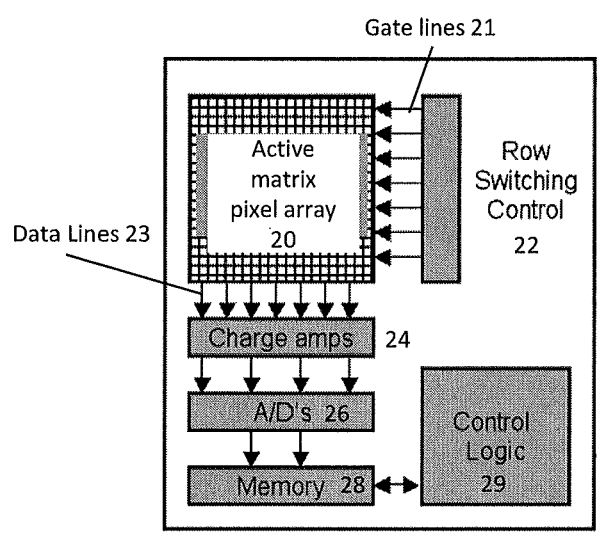
FIG. 2 illustrates a two-dimensional active matrix imaging array structure in accordance with the present disclosure.

FIG. 2 is a schematic diagram of the radiography detector system 14. The RDS 14 includes an active matrix pixel array 20 having a two-dimensional matrix of pixel elements where electronic charges generated directly or indirectly by incident x-rays are sensed and stored. In order to access the stored charge at each pixel, gate lines 21 are driven typically sequentially by a row switching control 22 causing all pixels in one row to output their stored charge onto data lines 23 that are coupled to charge amplifiers 24 at the end of each active matrix pixel array 20 column. The charge amplifiers 24 send the pixel charge data to analog-to-digital converters (A/D's) 26, where the analog signal is converted to a digital representation. The digital representation is then be stored in memory 28 awaiting transmission to the computer 16 at a time determined by the control logic 29. The charge amplifiers may also perform a multiplexing function in addition to their amplifying function.

Figure 3:
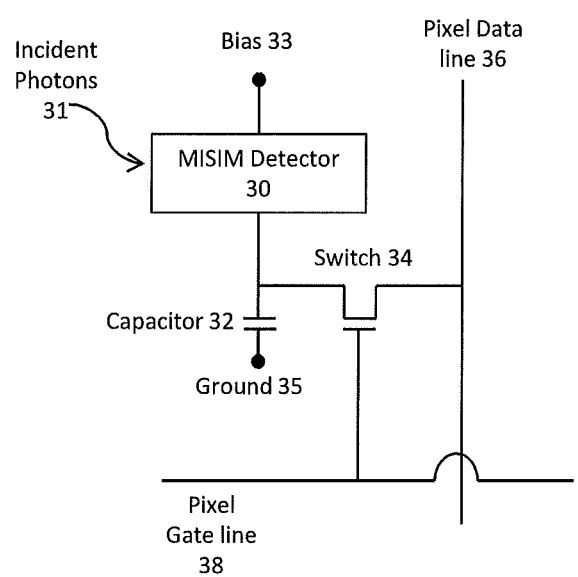
FIG. 3 illustrates a pixel circuit architecture in accordance with the present disclosure.

FIG. 3 is a schematic diagram of one embodiment of a pixel level circuit for one pixel in the active matrix pixel array 20 described in FIG. 2. The active matrix pixel array 20 typically contains a plurality of pixels. Within each pixel is a two terminal MISIM detector element 30 that absorbs the incident photons and generates electronic charge. A two terminal optional capacitor 32 stores the converted electronic charge and a readout circuit element, usually a three electrode thin film transistor (TFT) switch 34 transfers the electronic charge off the pixel. One electrode of the MISIM detector element 30 is connected to a high potential bias terminal 33 that is shared with other pixels in the active matrix pixel array 20 and one electrode of the capacitor 32 is connected to a low potential ground terminal 35 which is also shared with other pixels in the active matrix pixel array 20. The drain electrode of the TFT switch 34 is connected to the second electrode of the MISIM detector 30 and the second terminal of the capacitor 32. The source electrode of the TFT 34 is connected to the pixel data line 36, which is coupled to one of the plurality of data lines 23 described in FIG. 2. The gate electrode of the TFT 34 is connected to the pixel gate line 38, which is coupled to one of the plurality of gate lines 21.

Figure 4A:
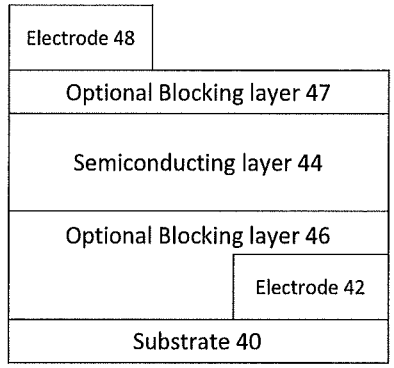
FIGS. 4a to 4e illustrate cross-sections of different embodiments of a Metal-Insulator-Semiconductor-Insulator-Metal (MISIM) detector element.

Turning to FIG. 4a, a schematic diagram of a first embodiment of a MISIM detector element 30 with the electrodes in a staggered configuration is shown. The detector element includes a substrate layer 40 atop which a first contact, or electrode, 42, is deposited or patterned. A first blocking layer 46 is deposited atop the substrate layer 40 encapsulating the first electrode 42. A semiconductor, or semiconducting, layer 44 is deposited atop the first blocking layer 46 and then a second blocking layer 47 deposited atop the semiconductor layer 44. As can be seen, the first and second blocking layers 46 and 47 are located on opposite surfaces of the semiconductor layer 44 from each other.

A second electrode 48 is deposited, or patterned, on to the second blocking layer 47. As shown in FIG. 4a, the first and second electrodes can be seen as being on opposite sides of the semiconductor layer 44. In some embodiments, the anti-reflective layer 49 is optional and is not necessary for operation of the MISIM detector element 30. However, in indirect conversion imaging, the anti-reflective layer 49 enhances performance by increasing the percentage of light photons impinging on the semiconducting layer 44 where photons are absorbed.

As can be seen in FIG. 4a, the first and second electrodes are staggered with respect to each other in a plane perpendicular to the semiconducting layer 44. In other words, with respect to the vertical detector of FIG. 4a, the first electrode is separated horizontally from the second electrode and does not overlap the second electrode in the vertical plane. In a preferred embodiment, the first and second electrodes do not overlap each other. Either one of the blocking layers may serve a dual function as a blocking layer and an anti-reflective layer.

In the current embodiment, one of the first or second contacts is coupled to either the first or second blocking layer or both. In some embodiments, where higher dark currents and lower EQEs are acceptable, either the first 46 or second 47 blocking layers or both may be replaced with ohmic and/or Schottky contacts. Besides X-ray digital imaging, other applications of the MISIM detector element could include biometric fingerprint imaging, touch displays and gesture displays. In biometric fingerprint imaging, the MISIM detector element is preferably sensitive to optical wavelengths and near infrared (600-900 nm) for multi-spectral imaging. In this embodiment, the thickness of the semiconductor layer 44 is selected so that the semiconductor layer can absorb infrared wavelengths along with optical wavelengths. Alternately, the semiconductor layer 44 could be replaced with a material having an enhanced sensitivity to infrared such as silicon nanowires, quantum dots, or other suitable inorganic or organic semiconducting material. For touch or gesture displays, because the MISIM detector element has a straightforward fabrication process and in a preferred embodiment, is directly compatible with large area thin film electronics processing, the MISIM detector element can be integrated directly into thin film LCD, OLED and LED displays to yield a high performance, cost-effective, display-sensor pixel unit.

Figure 4B:
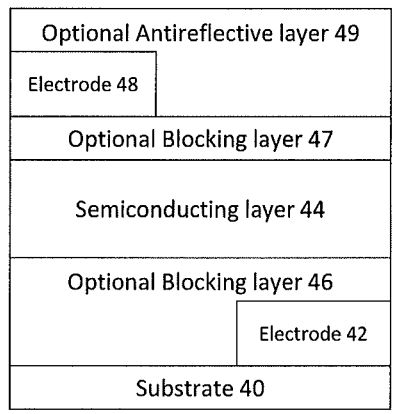

Turning to FIG. 4b, a schematic diagram of a second embodiment of a MISIM detector element 30 in a staggered configuration is shown. The detector element 30 includes a substrate layer 40 atop a first electrode 42 is deposited or patterned. A first blocking layer 46 is deposited atop the substrate layer 40 encapsulating the first electrode 42. A semiconductor layer 44 is deposited atop the first blocking layer 46 and then a second blocking layer 47 is deposited atop the semiconductor layer 44. As can be seen the first and second blocking layers 46 and 47 are located on opposite surfaces of the semiconductor layer 44 from each other.

A second electrode 48 is deposited, or patterned, on to the second blocking layer 47, which may be encapsulated by an antireflective layer 49. In the current embodiment, one of the first or second electrode is coupled to either the first or second blocking layer. In some embodiments, the anti-reflective layer 49 is optional and is not necessary for operation of the MISIM detector element 30. However, in indirect conversion imaging, the anti-reflective layer 49 enhances performance by increasing the percentage of light photons impinging on the semiconducting layer 44 where photons are absorbed.

As with the embodiment of FIG. 4a, the electrodes, may be seen to be staggered with respect to each other, both in the horizontal plane and the vertical plane. Again, in some embodiments, where higher dark currents and lower EQEs are acceptable, either of the blocking layers or both may be optional or can be replaced with ohmic and/or Schottky contacts.

Figure 4C:
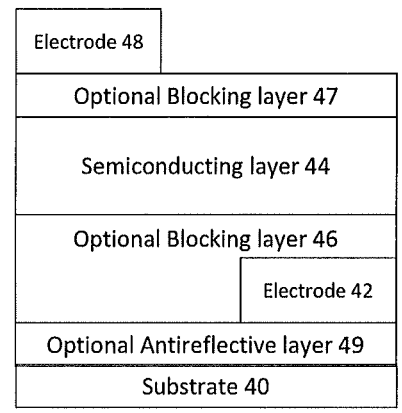

Turning to FIG. 4c, a schematic diagram of a third embodiment of a MISIM detector element 30 in a staggered configuration is shown. The detector element 30 includes a substrate layer 40 atop which an anti-reflective layer 49 may be deposited. As discussed with respect to FIG. 4b, the anti-reflective layer 49 is an optional layer. Atop the ant-reflective layer (or the substrate layer if no anti-reflective layer is present), a first electrode 42 is deposited or patterned. A first blocking layer 46 is deposited atop the anti-reflective 49 or substrate layer 40 encapsulating the first electrode 42. A semiconductor layer 44 is deposited atop the first blocking layer 46 and then the second blocking layer 47 is deposited atop the semiconductor layer 44. As can be seen the first and second blocking layers 46 and 47 are located on opposite surfaces of the semiconductor layer 44 from each other.

A second electrode 48 is deposited, or patterned, on to the second blocking layer 47. In the current embodiment, one of the first or second electrode is coupled to either the first or second blocking layer.

As with the embodiment of FIG. 4a, the electrodes, may be seen to be staggered with respect to each other, both in the horizontal plane and the vertical plane. Again, in some embodiments, where higher dark currents and lower EQEs are acceptable, either of the blocking layers or both may be optional or can be replaced with ohmic and/or Schottky contacts.

Figure 4D:
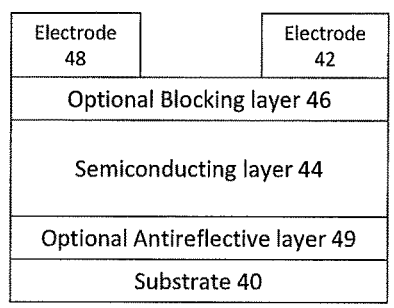

FIG. 4d shows a cross-section of a fourth embodiment of the MISIM detector element 30 in a top electrode configuration. In this embodiment, an optical anti-reflective layer 49 is deposited atop a substrate layer 40. A semiconductor layer 44 is then deposited atop the anti-reflective layer 49, or the substrate layer 40 if there is no anti-reflective layer. A blocking layer 46 is then deposited on the semiconducting 44. A pair of electrodes 42 and 48 are then deposited, or patterned, on the blocking layer 46. The pair of electrodes can be seen as being separated horizontally from each other.

Figure 4E:
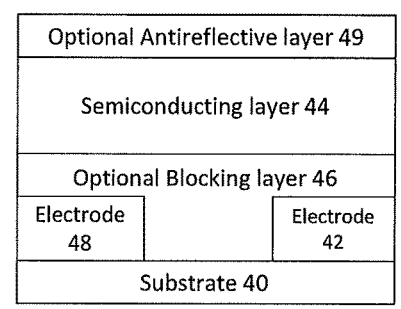

FIG. 4e shows a cross-section of a fifth embodiment of the MISIM detector 30 in a bottom electrode configuration. In this embodiment, first there is a pair of the patterned electrode 42 and 48 atop the substrate layer 40 followed by a blocking layer 46, a semiconducting layer 44 and the optional antireflective layer 49.

Dark current is a key problem with traditional MSM detectors because it reduces the detector dynamic range and image quality and is a function of the electric field applied on the bias contact 48. A large electric field is necessary for charge separation of the electronic carriers generated from the impinging photons on the semiconducting layer 44. If photocurrent can be maintained at a high level while dark current is reduced or alternately, a higher electric potential can be applied to the bias contact 48 to increase charge separation efficiency and correspondingly the photocurrent, without increasing the dark current, then a larger photo-to-dark current ratio is possible which equates to better dynamic range, higher contrast, higher quantum efficiencies and better digital images. Neither ohmic nor Schottky contacts for the bias 48 and sense 42 contacts have to date been able to achieve the dark current densities necessary for sensitive medical radiography imaging applications (around 10 pA/mm$^2$ or less). However, for less stringent applications (e.g. in the biometric fingerprint scanning or touch sensing domains), ohmic and Schottky contacts may suffice.

In one aspect of the disclosure, the present disclosure uses a staggered MISIM contact architecture coupled with blocking layers that simultaneously: (1) reduce dark current when there are no photons impinging on the semiconducting layer and (2) enable high photocurrents when photons impinge on the semiconducting layer. Insulating contacts were typically not considered viable because of the anticipated slow response times and the potential for charge build-up on the insulating layer that can lead to reliability concerns.

To achieve these two goals, in the current disclosure, the material of the blocking layers 46 and 47 is carefully selected in order to: provide a low trap density interface with the semiconducting layer, prevent or reduce injection of charge carriers to the semiconducting layer from bias and sense electrode (e.g. have wide band-gap), and to have a dielectric strength such that it can be operated in soft (reversible) breakdown during device operation repeatably when the applied bias and blocking layer 46 thickness are optimized to take into account both the dark conductivity and photoconductivity of the semiconducting layer 44 which is also a function of semiconducting layer 44 thickness, applied electric bias and material properties.

When photons are impinging on the semiconducting layer 44 thereby causing the resistivity of the semiconducting layer 44 to decrease, the blocking layer 46 operates in soft (i.e. reversible) breakdown mode allowing a vertical conduction path from bias 48 and sense contacts 42 through the blocking layer 46 to the semiconducting layer 44. Operating in soft breakdown allows for conduction through the blocking layer 46 which can overcome the response time challenge while still maintaining a low dark current by limiting bias 48 and sense 42 contact injection currents. Using a blocking layer 46 that is too thick or with a high dielectric breakdown strength can yield poor results or alternately, choice of an incompatible blocking layer 46 material can yield a poor interface with the semiconducting layer 44 so that traps and defects cause a drop in MISIM detector 30 quantum efficiency.

With the embodiments of FIGS. 4a and 4b, the staggered design is enhanced when insulating blocking contacts are employed because there is need for a high voltage to be applied to the sensor bias 48 contact. Putting the bias contact 48 further away from the TFT (i.e. on top of the semiconducting layer 44 while the TFT and sense contact 42 are on the bottom side of the semiconducting layer 44 thus helps improve sensor and TFT reliability and reduces any excess leakage current corrupting the sensor signal due to the bias contact 48.

In experiments, it was determined that using a 450 nm amorphous silicon semiconducting layer 44 works well with a polyimide blocking layer 46 of 200 nm. The blocking layer 47 can also be a 200 nm polyimide blocking layer. This combination yields an interface with high EQE (above 65%) for green light. Alternately, if high external quantum efficiency is required for blue light, then, for the same amorphous silicon and polyimide material combination, the semiconducting layer 44 thickness may need to be reduced which requires a corresponding re-optimization of the blocking layer thickness 46. If the semiconducting layer 44 is changed from amorphous silicon to a metal oxide like IGZO (Indium Gallium Zinc Oxide) or even polysilicon, both of which have different material properties and absorption coefficients, the choice of blocking layer material (for interface purposes), thickness and maximum bias voltage applied may be reconsidered or re-optimized via calculation prior to manufacturing. Additional improvements in EQE are possible if an optional anti-reflective layer such as amorphous silicon nitride is used on top of the semiconducting layer directly in the path of the incident photons.

Moreover, it is noted that it is possible to pattern the blocking layer 46 and use either insulating contacts for both the bias 48 and sense 42 contacts or alternately, use an insulating contact for just one contact (e.g. either for the bias contact 48 or for the sense 42 contact depending on the bias used).

A patterning process (e.g. of the bias 48 or sense 42 contacts or the blocking layer 46) can also potentially degrade the semiconducting layer 44 interface because of exposure to air and chemicals during the patterning process. Typically though, as shown in FIGS. 4a to 4d, a blocking layer running across both bias 48 and sense 42 contacts provides an improved interface with the semiconductor layer 44 with fewer defects and traps as well as encapsulating the semiconducting layer 44 thus maintaining higher quantum efficiency. In an alternative embodiment, MISIM detector elements where only one of the bias 48 or sense 42 contacts is insulated may be used if careful semiconductor processing is undertaken.

Moreover, as noted, the bias 48 and sense 42 contacts, can be placed, one each on opposite sides of the semiconducting 44 layer as long as they are separated by a horizontal distance so that photon absorption and transport remains in the horizontal (lateral) direction. Furthermore, if bias 48 and sense 42 contacts are made using transparent materials, both the top electrode or bottom electrode configuration can detect light photons equally well from either direction. Transparent materials include, but are not limited to, aluminium, molybdenum, chromium, indium tin oxide (ITO), zinc oxide (ZnO), indium gallium zinc oxide (IGZO), and poly (3,4-ethylenedioxythiophene) polystyrene sulfonate (PEDOT:PSS).

Figure 5:
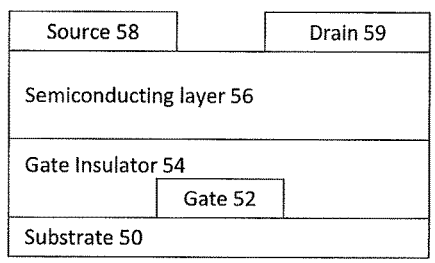
FIG. 5 illustrates a cross-section of a bottom-gate and top-gate thin film transistor (TFT) configuration in accordance with the present disclosure.
Figure 5:
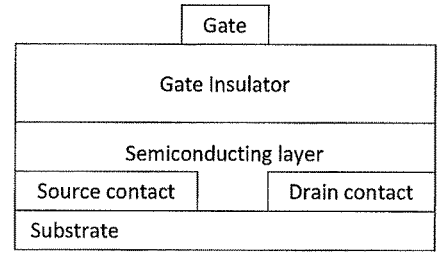

FIG. 5a shows a bottom gate, inverted staggered thin film transistor (TFT) structure where a substrate 50 (e.g. glass or plastic) contains a patterned gate electrode 52, followed by a gate insulator 54, a semiconducting layer 56 and a patterned contact layer defining the source 58 and drain 59 contacts. FIG. 5b shows a top gate, inverted staggered TFT structure with the layers in a reverse configuration. Both are implementations of amorphous silicon TFTs in use by the display industry today. Similar cross-sections can be drawn for CMOS (complementary metal-oxide-semiconductor), IGZO and polysilicon transistors as understood by one skilled in the art.

The photoconductive element implementation shown in at least one of FIGS. 6a to 6g can be mapped onto the pixel circuit shown in FIG. 3, where the transistor gate electrode 63 is connected to the pixel gate line 38, the source electrode 61 is connected to the pixel data line 36 (see FIG. 3) and the bias electrodes 67 are connected to the bias node 33. Since the MISIM detector element has an intrinsic internal capacitance between the sense 66 and bias 67 electrodes as discussed earlier, the capacitor 32 shown in FIG. 3 is optional. Moreover FIGS. 6a to 6g can be mapped onto other pixel readout circuits such as active pixel sensors or photon counting circuits as would be understood by one skilled in the art.

One additional challenge with placing the TFT readout circuit element underneath the MISIM detector element is that the normal operating voltage on the bias 67 and/or sense 66 electrodes can influence TFT operation especially if a bottom gate TFT configuration is employed as is the case in at least one of FIGS. 6a to 6g. Here, a back gate 75 (e.g. preferentially coupled to the gate electrode 63 to minimize leakage current) is included to ensure the TFT does not conduct inadvertently due to one of the electrodes on top. If a top gate TFT configuration is employed, the need for the back gate 75 can be mitigated since the top gate will act as an electrostatic shield and reduce the likelihood of or prevent the bias 67 or sense 66 electrodes from inadvertently biasing the TFT ON.

In the device architecture shown in at least one of FIGS. 6a to 6g, the scintillating layer 68 (akin to the scintillator 15) is deposited or placed on top of the MISIM detector element due to the semiconducting layer 70 being exposed fully to incident light from the scintillating layer 68 resulting in a higher absorption of incident light and thus, better EQE. If the scintillating layer 68 is deposited or placed on the bottom (i.e. adjacent to the glass 60), then there could be a loss of spatial resolution due to the thickness of the glass 60 and loss in EQE if the sense and bias electrodes are opaque and block light from reaching the amorphous silicon 70 semiconducting layer. Also, since the photoconductive element disclosed does not use a p+ doped layer like the PIN photodiode, blue light emitting scintillating phosphors can work.

Figure 6A:
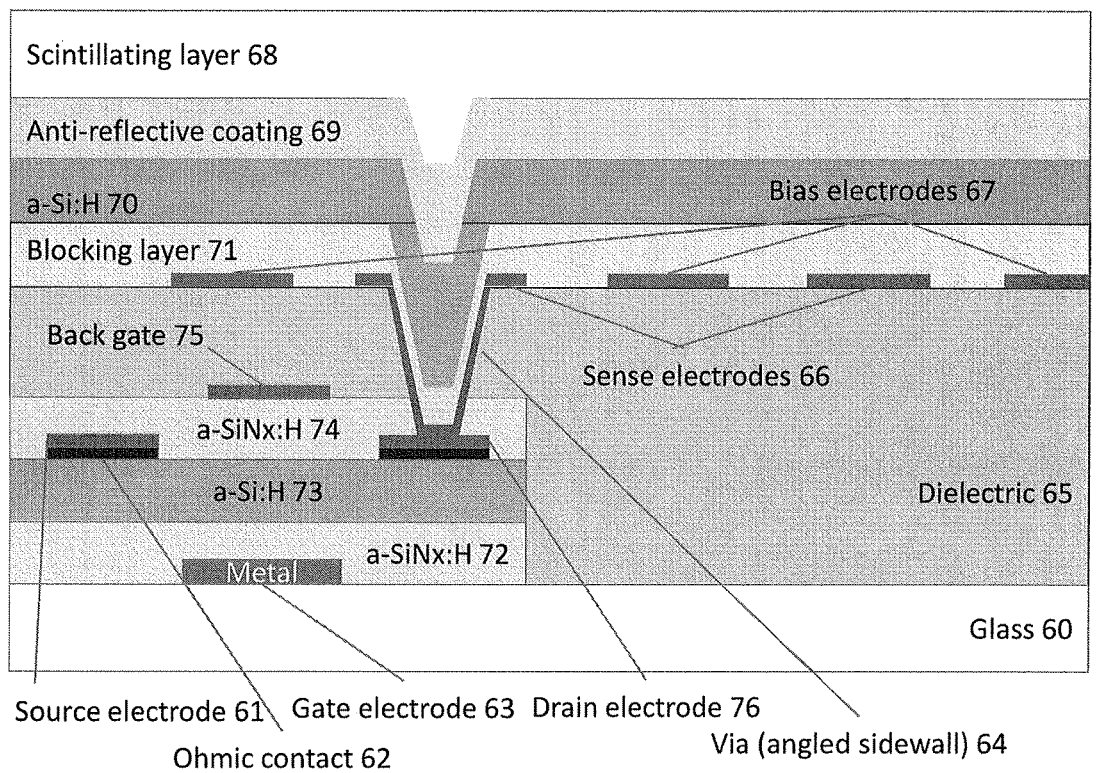
FIGS. 6a to 6g illustrate different cross-sections of photoconductive element implementation using a MISIM detector element placed on top, bottom and side (co-planar configuration) of a readout circuit element in accordance with the present disclosure
Figure 6B:
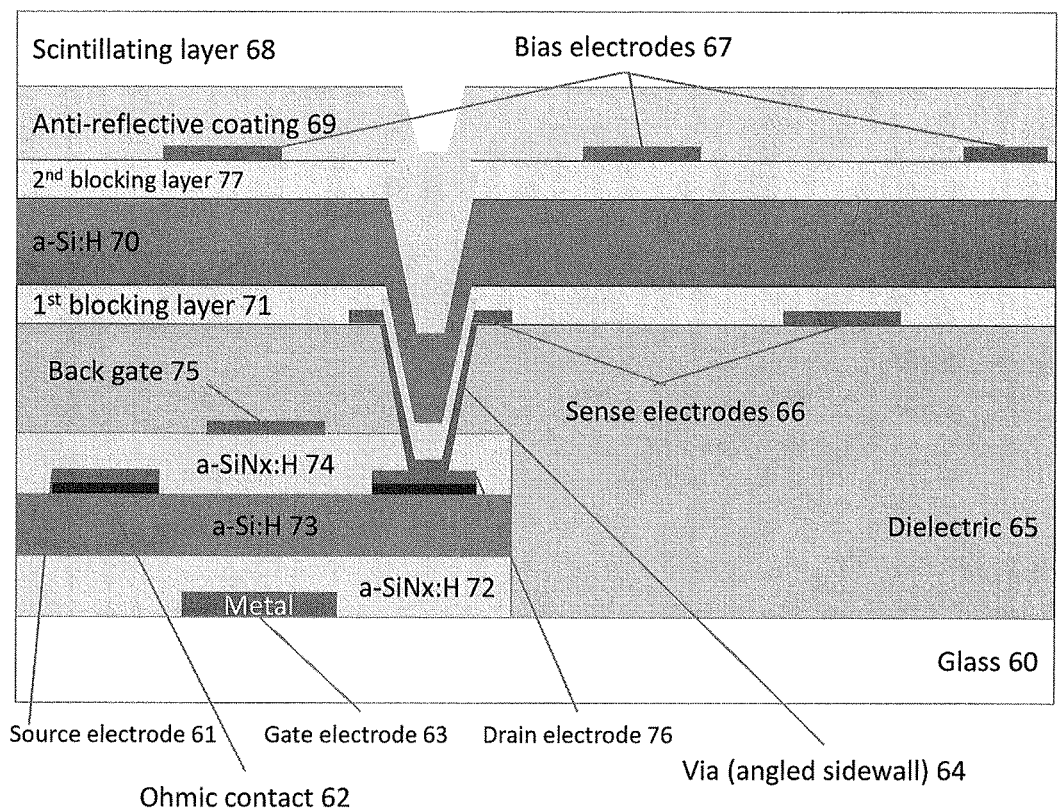
Figure 6C:
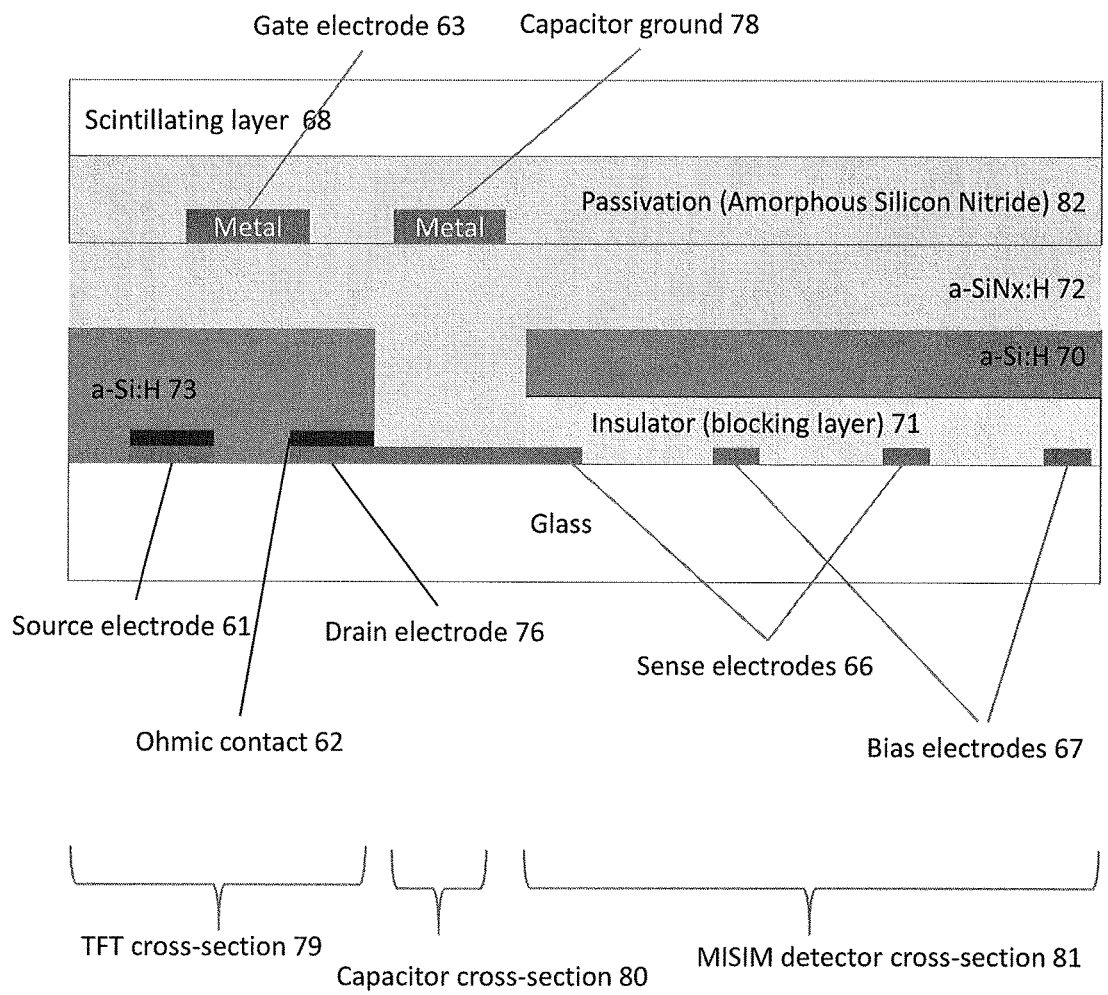

The implementation shown in FIGS. 6a and 6b uses a bottom gate TFT underlying the bottom electrode and staggered electrode MISIM detector respectively. The implementation shown in FIG. 6c uses a top gate TFT and bottom electrode MISIM detector in co-planer configuration. The implementation shown in FIGS. 6d and 6e uses a top gate TFT underlying the bottom electrode and staggered electrode MISIM detector respectively. FIGS. 6f and 6g show two possible implantations of fabricating the readout circuit element on top of the MISIM detector element. FIG. 6f uses a top electrode MISIM detector and top gate TFT where FIG. 6g uses a top electrode MISIM detector and bottom gate TFT switch. It should be noted that additional implementations are possible that use a combination of either a top or bottom gate TFT switch and a top or bottom or staggered electrode MISIM detector in both co-planar or fully overlap configuration (MISIM detector over TFT or TFT over MISIM detector). Moreover, use of transparent sense 66 and bias 67 electrodes can also enable top, bottom and staggered electrode MISIM detectors to be used interchangeably with comparable performance.

FIG. 6a shows a cross-section of a photoconductor element implemented using a readout circuit element embedded physically underneath the amorphous silicon MISIM detector element. The MISIM detector element includes sense 66 and bias 67 electrodes in a comb configuration, a polyimide blocking layer 71 (or alternately, among others, any wide band-gap organic/nonorganic insulator such as, but not limited to, amorphous silicon nitride, amorphous silicon oxide, amorphous silicon oxynitride, benzocyclobutene (BCB), parylene, polystyrene or any n/p-type organic/nonorganic blocking layer such as PTCBI, CuPc) that covers at least one of the sense 66 or bias 67 electrodes, an amorphous silicon (a-Si:H) semiconducting layer 70 (or alternately, molybdenum sulphide, Indium Gallium Zinc Oxide, polycrystalline silicon, amorphous selenium, mercuric iodide, lead oxide, microcrystalline silicon, nanocrystalline silicon, crystalline silicon, pentacene, PTCBI, CuPc, small molecule organic semiconductor, or polymer organic semiconductor) and an optional anti-reflective coating layer 69 e.g. amorphous silicon nitride (a-SiNx:H).

The readout circuit element shown employs a bottom gate amorphous silicon TFT acting as a switch. The TFT includes an amorphous silicon nitride (a-SiNx:H) gate dielectric layer 72, an amorphous silicon (a-Si:H) semiconducting layer 73, an a-SiNx:H 74 passivation layer and a doped ohmic contact layer 62.

Alternately, the readout circuit element could employ a variety of active pixel sensor or photon counting pixel readout circuits. Active pixel circuits include an on-pixel preamplifier circuit in place of the TFT switch circuit 34 shown in FIG. 3.

The MISIM detector element has a lower intrinsic capacitance than a comparably sized PIN photodiode due to the intrinsic capacitance that arises between the sense 66 and bias 67 electrodes, which are placed further apart (e.g. 5 um) in contrast to a PIN photodiode (e.g. 1 um). In particular, the lower capacitance of the MISIM detector element (here around 0.2 pF for a 100 micron pixel) as compared to PIN photodiodes (typically around 1 pF for a 100 micron pixel) makes the combination of a MISIM detector element with an active pixel sensor readout element superior in terms of signal-to-noise ratio (SNR). The SNR improvement occurs because the input charge to voltage gain of the MISIM detector element is proportionally higher than if a PIN diode is employed due to the proportionally lower capacitance of the MISIM detector element.

Embedding the readout circuit element underneath the MISIM detector element also has the advantages of increasing or maximizing the light absorption area. This becomes more important because active pixel sensor circuits typically use more than one transistor in the readout circuit element in contrast to a switch 34 that requires just one TFT. Thus, embedding the readout circuit element under the MISIM detector element is beneficial to maximize performance and EQE.

The TFT drain electrode 76 is connected by a via 64 in an interlevel dielectric 65 to one of the sense electrodes 66 where the dielectric 65 physically separates the MISIM detector element and the readout circuit element. The dielectric can be chosen from a variety of materials including amorphous silicon nitride, amorphous silicon oxide, amorphous silicon oxynitride, polyimide, benzocyclobutene (BCB), parylene, acrylic, and polystyrene or other common inorganic or organic dielectrics.

The choice of the dielectric 65 is important particularly because using a MISIM detector element requires the use of potentially high voltages due to insulating contacts. A high voltage on the bias 67 or sense 66 electrodes can give rise to high vertical electric field between the TFT electrodes (e.g. back gate 75, source 61 or drain 76) leading to local breakdown of the dielectric 65.

However, each material has a different dielectric strength and breakdown voltage and correspondingly requires tuning of layer thickness. This design for high voltage resilience is in addition to the traditional design process undertaken to optimize an interlevel dielectric to serve as a planarization layer and as a low-k dielectric to reduce parasitic coupling capacitance. For example, if BCB is used for the dielectric 65 with a breakdown voltage of 1 MV/cm, and the bias 67 electrodes are set to a potential of 500V, then at least 5 um of BCB are necessary to prevent accidental dielectric 65 breakdown. The thickness of BCB required is now well beyond the thickness used typically for an interlevel dielectric in the TFT industry. Using very thick layers of dielectric 65 requires overcoming integration challenges between the detector element and readout circuit element.

The amorphous silicon MISIM detector element shown in FIG. 6a works well if the bias 67 and sense 66 electrode layers are made thin (e.g. 50-100 nm) to avoid step coverage issues for the follow-on blocking layer 71 and semiconducting 70 layers. Here, for example, a 5 um thick dielectric 65 layer underneath the MISIM detector element may cause a functional (EQE loss) and reliability (poor connectivity) problem if the via is made in the traditional process with steep sidewall angles. So, to allow for proper continuity and coverage, the via 64 in the dielectric 65 can have a sloped or angled sidewall. For BCB, an angle of 45 degrees or shallower was discovered to work appropriately for this task although other sidewall angles and sense 66 and bias 67 electrode thickness combinations can also work by proper design as would be understood by one skilled in the art.

FIG. 6b shows a cross section of an alternative integration of MISIM detector with underlying readout circuitry. In order to increase the reliability and decreasing the chance of dielectric 65 breakdown (due to the use of potentially high voltages at the bias contact), the staggered electrode configuration for MISIM detector (FIG. 4b) has been used. It should be noted that the placement of the sense 66 and bias electrode 67 is preferred to be in a way that the vertical electric field between the bias electrode and the underlying TFT is at a reduced or minimum value. In one embodiment, the sensing electrode may be used to mask-out the electric field for the underlying TFT and line. Thus, the size of the TFT, the area of the pixel, the choice of the dielectric 65 and its thickness, the choice of the $1^{st}$ and $2^{nd}$ blocking layers 71 and 77 and the thickness of the semiconducting layer (e.g. a-Si:H) 70 affect the width and the spacing of the sense electrodes 66 and bias electrodes 67. FIG. 6c shows a cross-section of a photoconductor element using a co-planar implementation. The element components can be mapped to the pixel level circuit shown in FIG. 3, which includes an amorphous silicon MISIM detector element 30, a capacitor 32 and an amorphous silicon TFT switch 34. In FIG. 6c, the MISIM detector cross-section 81 contains bias electrodes 67 and sense electrodes 66 in a commonly known comb electrode configuration along with a polyimide blocking layer 71 (or alternately, among others, any wide band-gap organic/nonorganic insulator such as: amorphous silicon nitride, amorphous silicon oxide, amorphous silicon oxynitride, benzocyclobutene (BCB), parylene, polystyrene or any n/p-type organic/non-organic blocking layer such as PTCBI, CuPc), a semiconducting layer of amorphous silicon 70 (or alternately, one or more of molybdenum sulphide, Indium Gallium Zinc Oxide, polycrystalline silicon, amorphous selenium, mercuric iodide, lead oxide, microcrystalline silicon, nanocrystalline silicon, crystalline silicon, PTCBI, or CuPc), an amorphous silicon nitride layer 72 and a further amorphous silicon nitride passivation layer 82. The capacitor cross-section 80 shows the bottom plate shared with the sense electrode 66 along with a top capacitor plate connected to ground 78, typically a low electric potential. The capacitor dielectric in this case is amorphous silicon nitride 74, and is shared with the anti-reflective layer in the MISIM detector cross-section 81. The TFT cross-section 79 includes a source electrode 61 connected to the pixel data line 36 from FIG. 3. Also shown is a gate electrode 63 connected to the pixel gate line 38 in FIG. 3. The drain electrode 76 is connected to the sense electrodes 66 and forms one plate of the capacitor shown in the capacitor cross-section 80. For the TFT cross-section 79, an amorphous silicon layer 73 is the active layer and this can be shared with the MISIM detector cross-section 81. The TFT gate dielectric is formed by an amorphous silicon nitride layer 74, which can be shared with the anti-reflective layer shown in the MISIM detector's cross-section 81 and the capacitor's dielectric layer.

One of the benefits of the co-planar design shown in FIG. 6c allows for shared uses of multiple layers, for example, the TFT gate dielectric can serve as an anti-reflective coating for the MISIM detector 30 (FIG. 3). In contrast, in a PIN diode, the unique amorphous silicon PIN isolation process and the thick semiconductor layer required to absorb green photons typically precludes sharing of any layers except metal contacts. In addition, the PIN diode sidewalls need to be etched carefully and passivated to reduce excess leakage current. In the MISIM detector 30 (FIG. 3), because the conduction path is horizontal, the horizontal interface is primarily important. As described earlier, using the blocking layer 46 helps protect the interface to the semiconducting layer 44. Thus, device performance remains stable in the long term even if the MISIM detector 30 is built in a standard TFT switch 34 manufacturing process. It should be noted that the co-planar design of FIG. 6c can also be adapted to use the staggered sensor described in FIGS. 4a and 4b.

Figure 6D:
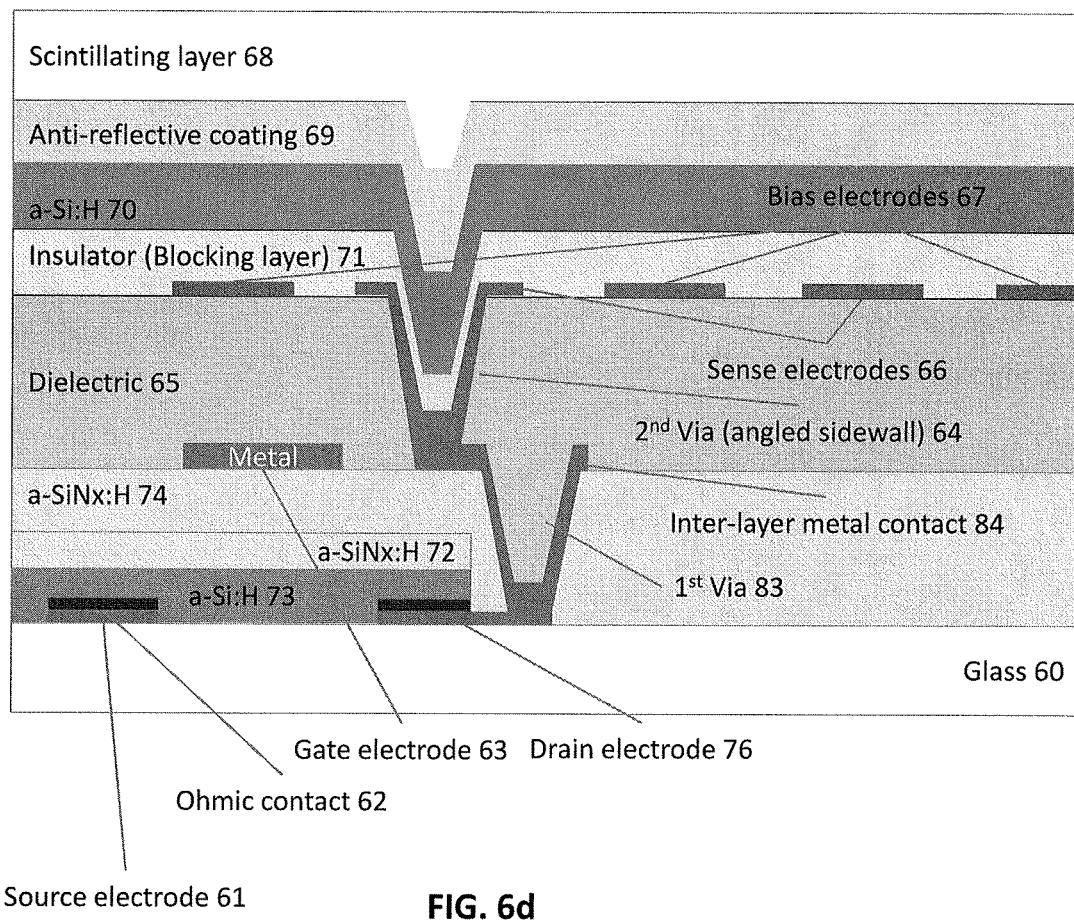
Figure 6E:
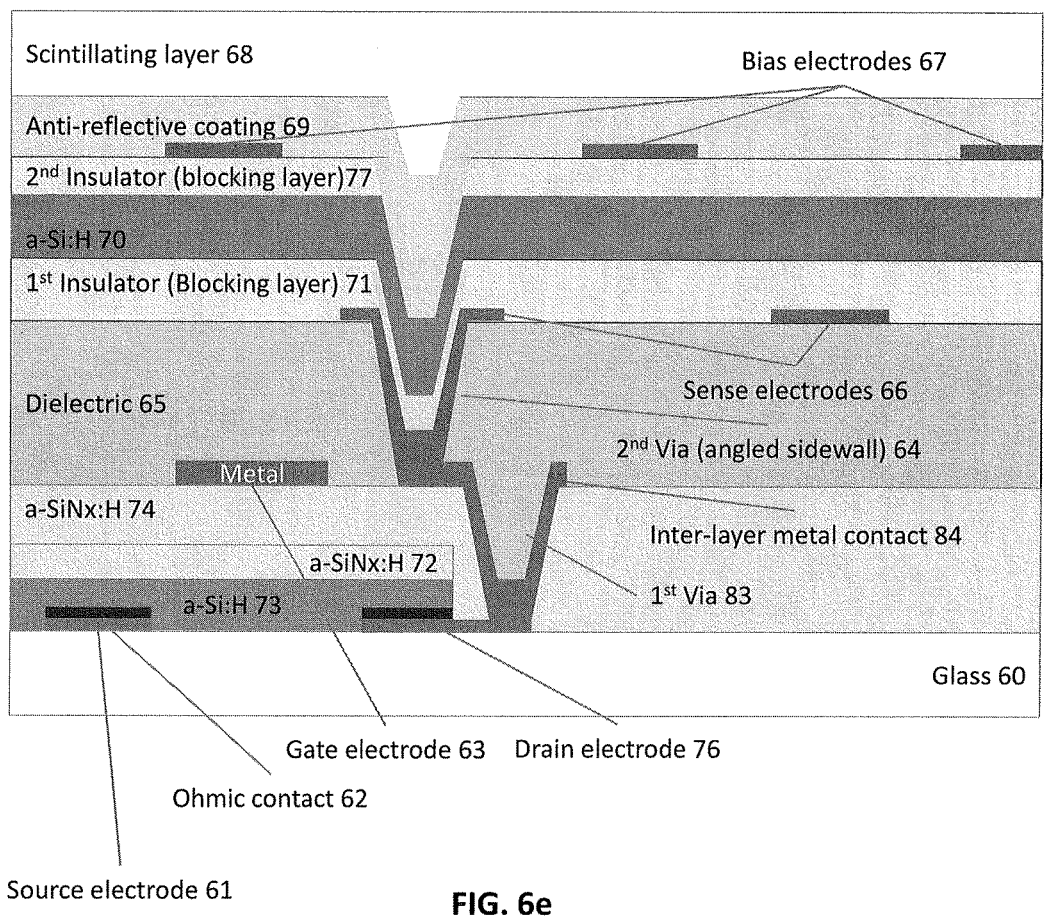
Figure 6F:
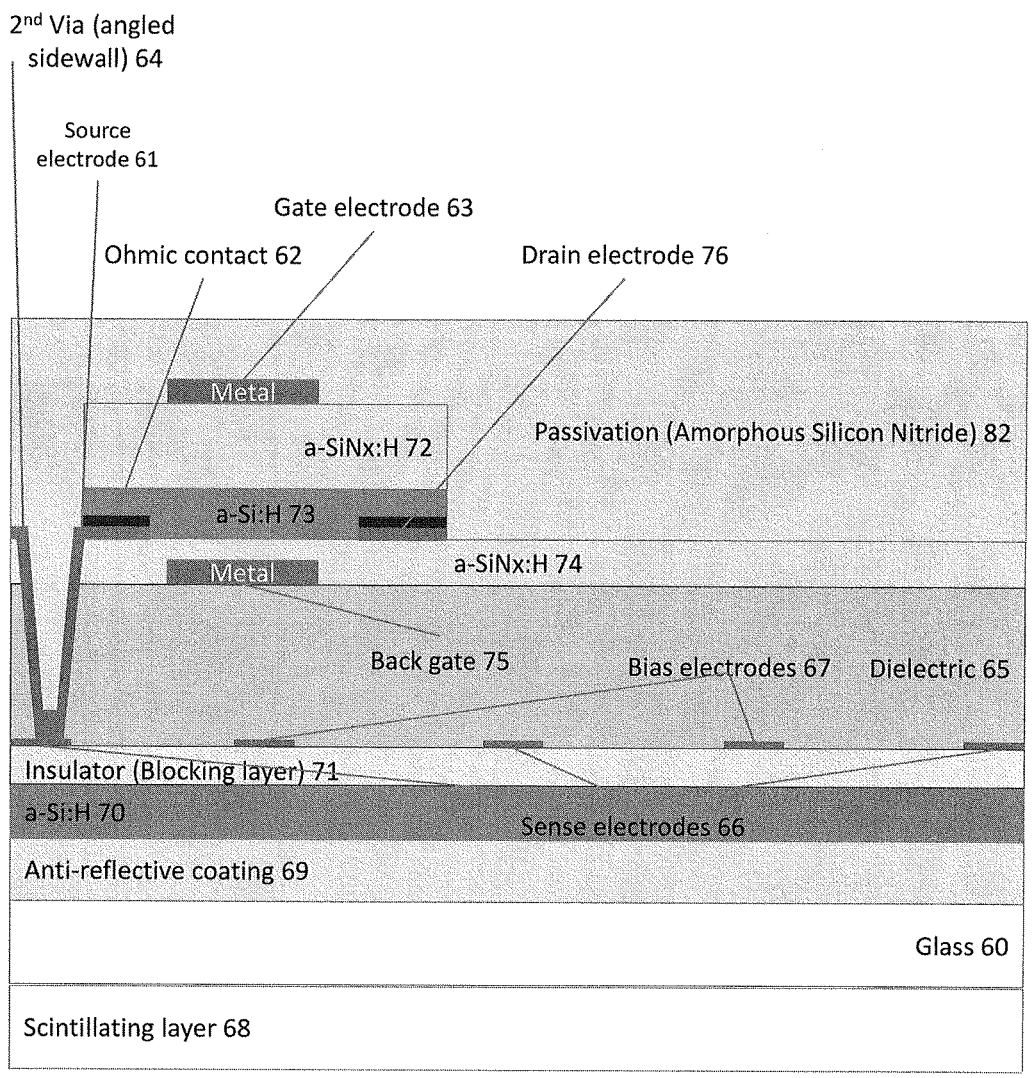
Figure 6G:
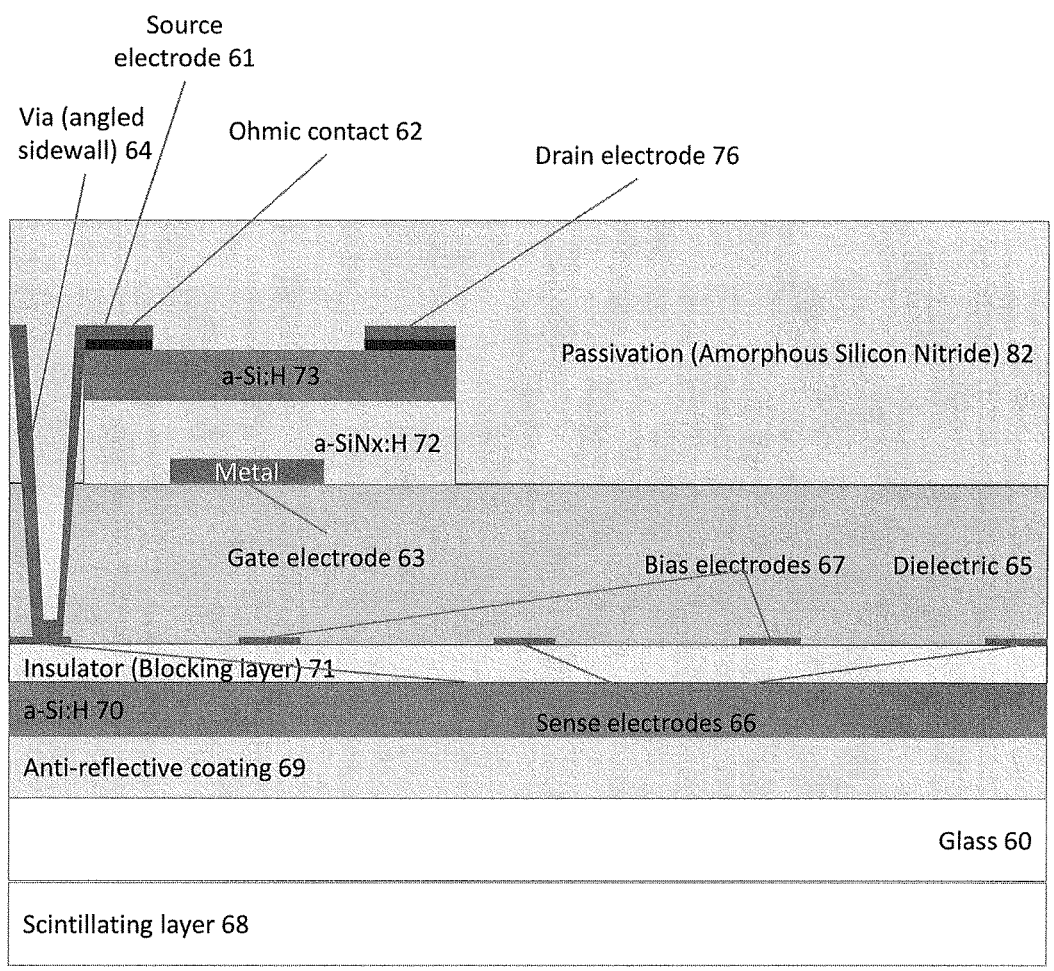

FIGS. 6d and 6e are two other possible integrations of the MISIM detector 30 with the TFT switch 34. FIGS. 6d and 6e shows a cross section of the implantation of the top gate TFT underneath the bottom and staggered electrode MISIM detector respectively. As it is shown in FIGS. 6d and 6e, these two designs may require inter-layer metal contact in order to connect the MISIM detector 30 to the TFT switch.

Figure 7:
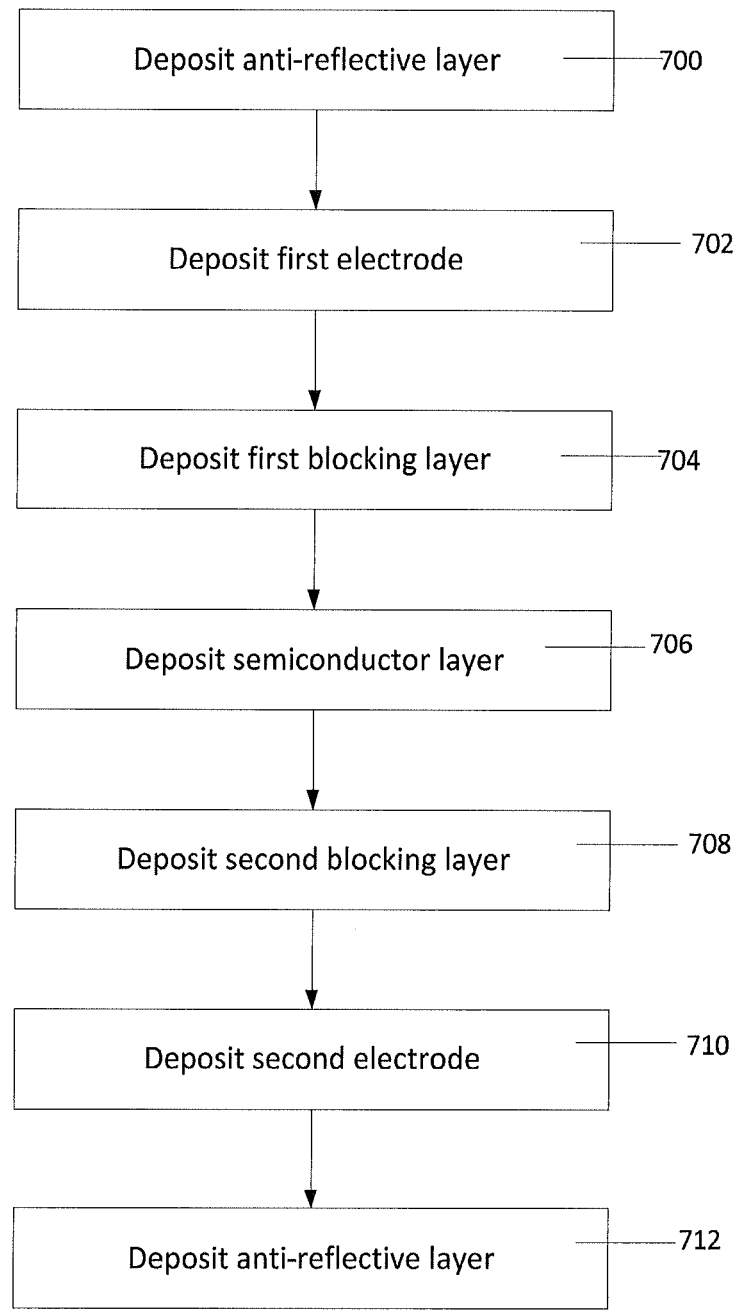
FIG. 7 is a flowchart outlining a method of producing a detector element.

Turning to FIG. 7, a flowchart outlining a method of detector element manufacture is shown. Initially, atop a substrate, an anti-reflective layer is deposited atop a substrate layer (700). It will be understood that this is optional depending on the design of the detector element. A first electrode is then deposited atop the substrate layer or the anti-reflective layer (702) depending on detector element design.

A first blocking layer is then deposited atop the first electrode (704). As with the anti-reflective layer, the first blocking layer may be optional depending on the design of the detector element. A semiconductor layer is then deposited on the first blocking layer or the first electrode (706).

A second optional blocking layer can then be deposited atop the semiconductor layer (708). A second electrode is then deposited atop the second blocking layer or the semiconductor layer, depending on the design of the detector element (710).

In accordance with the disclosure, the first and second electrodes are located on opposite sides of the semiconductor layer and are staggered with respect to each other in a plane perpendicular to the semiconductor layer. In a preferred embodiment, the first and second electrodes are staggered such that they do not overlap each other.

Finally, another optional anti-reflective layer may be deposited atop the second electrode (712).

In the preceding description, for purposes of explanation, numerous details are set forth in order to provide a thorough understanding of the embodiments. However, it will be apparent to one skilled in the art that these specific details may not be required. In other instances, well-known structures may be shown in block diagram form in order not to obscure the understanding. For example, specific details are not provided as to whether elements of the embodiments described herein are implemented as a software routine, hardware circuit, firmware, or a combination thereof.

Embodiments of the disclosure or components thereof can be provided as or represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor or controller to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor, controller or other suitable processing device, and can interface with circuitry to perform the described tasks.

The above-described embodiments are intended to be examples only. Alterations, modifications and variations can be effected to the particular embodiments by those of skill in the art without departing from the scope, which is defined solely by the claims appended hereto.

What is claimed is:
1. A detector element for a digital imaging system comprising:
 a semiconductor layer for absorbing photons;
 a first electrode located on a first side of the semiconductor layer; and a second electrode located on a second side of the semiconductor layer, the first and second side on opposite sides of the semiconductor layer;

wherein the first and second electrodes are staggered with respect to each other along a plane perpendicular to the semiconductor layer and do not overlap each other along a plane perpendicular to the semiconductor layer.

2. The detector element of claim 1 further comprising a blocking layer between said first electrode and said semiconductor layer.

3. The detector element of claim 2 further comprising a blocking layer between said second electrode and said semiconductor layer.

4. The detector element of claim 2 wherein said blocking layer comprises at least one of an insulating, ohmic or Schottky layer.

5. The detector element of claim 4 wherein the insulating layer is at least one of amorphous silicon nitride, amorphous silicon oxide, amorphous silicon oxynitride, polyimide, benzocyclobutene (BCB), poly-(N-vinyl carbazole) (PVK), parylene, acrylic, and polystyrene.

6. The detector element of claim 2 wherein said blocking layer also functions as an antireflective layer.

7. The detector element of claim 1 further comprising an antireflective layer located on at least one side of said first or second electrodes.

8. The detector elements of claim 7 wherein said antireflective layer is at least one of amorphous silicon nitride, amorphous silicon oxide, amorphous silicon oxynitride or organic material.

9. The detector element of claim 1 wherein said electrodes are at least one of opaque or transparent conductive materials.

10. The detector element of claim 1 wherein said detector element is coupled to a readout circuit element.

11. The detector element of claim 10 where the readout circuit element comprises at least one of a transistor switch circuit, an active pixel sensor circuit or a photon counting pixel circuit.

12. The detector element of claim 10 wherein the detector element is integrated with a display pixel.

* * * * *